(12) United States Patent
Rousseau

(10) Patent No.: US 6,685,714 B2
(45) Date of Patent: Feb. 3, 2004

(54) METHOD FOR DEPLOYING MEDICAL TEXTILES

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 161 days.

(21) Appl. No.: 09/938,404

(22) Filed: Aug. 24, 2001

(65) Prior Publication Data

US 2002/0052622 A1 May 2, 2002

Related U.S. Application Data

(62) Division of application No. 09/443,882, filed on Nov. 19, 1999, now Pat. No. 6,302,897.

(51) Int. Cl.⁷ .............................................. A61B 17/08
(52) U.S. Cl. ..................................... 606/151; 128/898
(58) Field of Search ................................ 606/151, 190, 606/213; 128/898; 623/11.11; 604/27, 36, 158, 152, 13, 15, 9, 191, 200

(56) References Cited

U.S. PATENT DOCUMENTS

| 4,685,447 A | | 8/1987 | Iversen et al. | |
| 4,854,316 A | * | 8/1989 | Davis | 606/153 |
| 5,176,692 A | | 1/1993 | Wilk et al. | |
| 5,366,460 A | * | 11/1994 | Eberbach | 606/151 |
| 5,368,602 A | | 11/1994 | de la Torre | |
| 5,379,754 A | * | 1/1995 | Tovey et al. | 600/109 |
| 5,383,477 A | * | 1/1995 | DeMatteis | 128/898 |
| 5,464,403 A | * | 11/1995 | Kieturakis et al. | 606/1 |
| 5,514,153 A | | 5/1996 | Bonutti | |
| 5,681,342 A | | 10/1997 | Benchetrit | |
| 5,824,082 A | | 10/1998 | Brown | |
| 5,836,961 A | | 11/1998 | Kieturakis et al. | |
| 5,865,728 A | | 2/1999 | Moll et al. | |
| 5,871,498 A | | 2/1999 | Jervic et al. | |
| 5,893,866 A | | 4/1999 | Hermann et al. | |
| 6,015,421 A | | 1/2000 | Echeverry | |
| 6,224,616 B1 | * | 5/2001 | Kugel | 606/151 |
| 6,287,344 B1 | * | 9/2001 | Wampler et al. | 623/23.72 |

FOREIGN PATENT DOCUMENTS

| WO | WO 9600531 A1 | 1/1996 |
| WO | WO 97/21461 A1 | 6/1997 |

* cited by examiner

Primary Examiner—Eduardo C. Robert

(57) ABSTRACT

A thermoformed bladder is disclosed for assisting in the application of prosthetic mesh devices. The unit is fabricated from two layers of film that have been thermoformed in one localized region and then sealed. The sealed unit has air trapped within the three dimensional portion which can be forced into the non-formed region causing the non-formed region to expand and apply force against the prosthesis to assist in deployment.

1 Claim, 3 Drawing Sheets

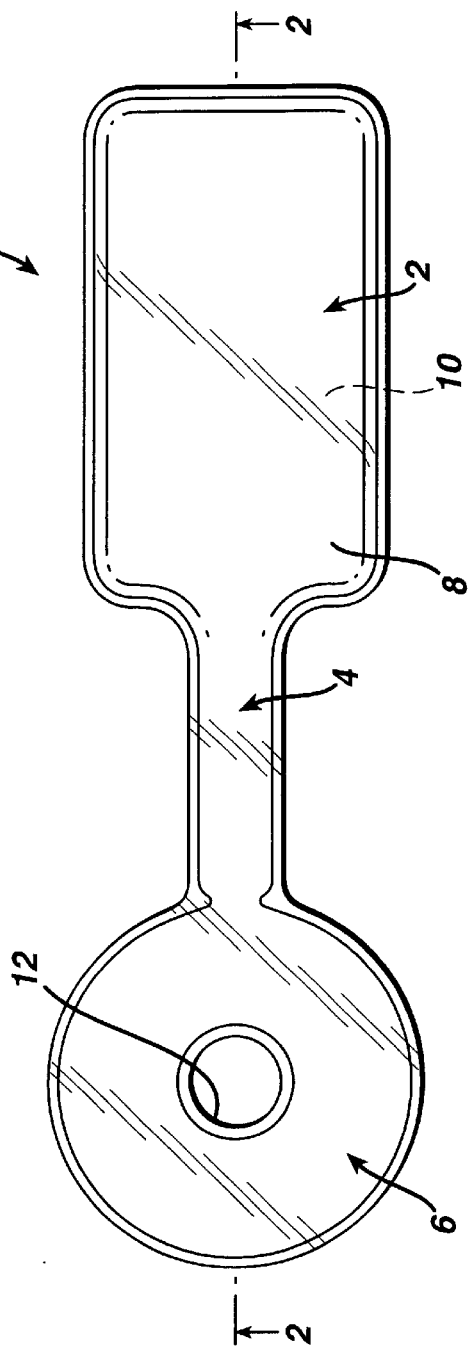

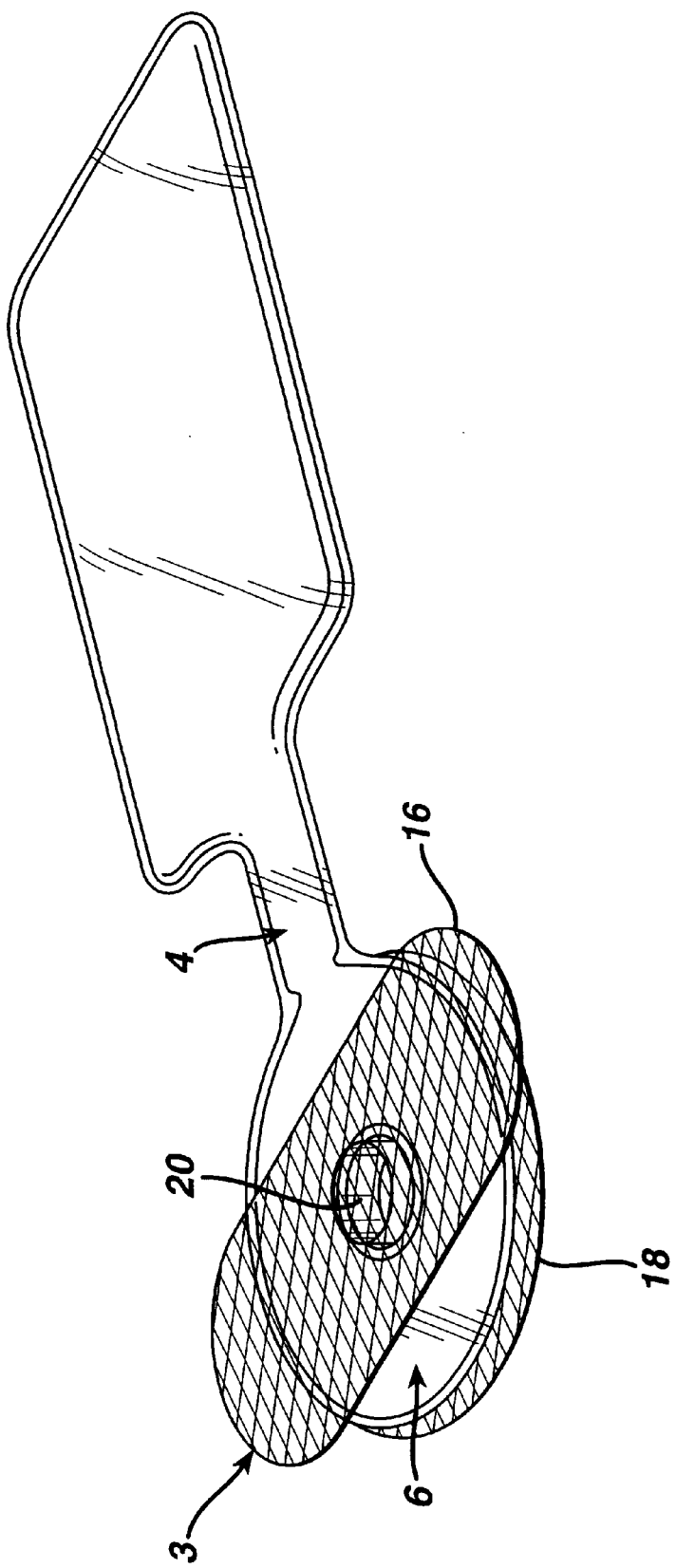

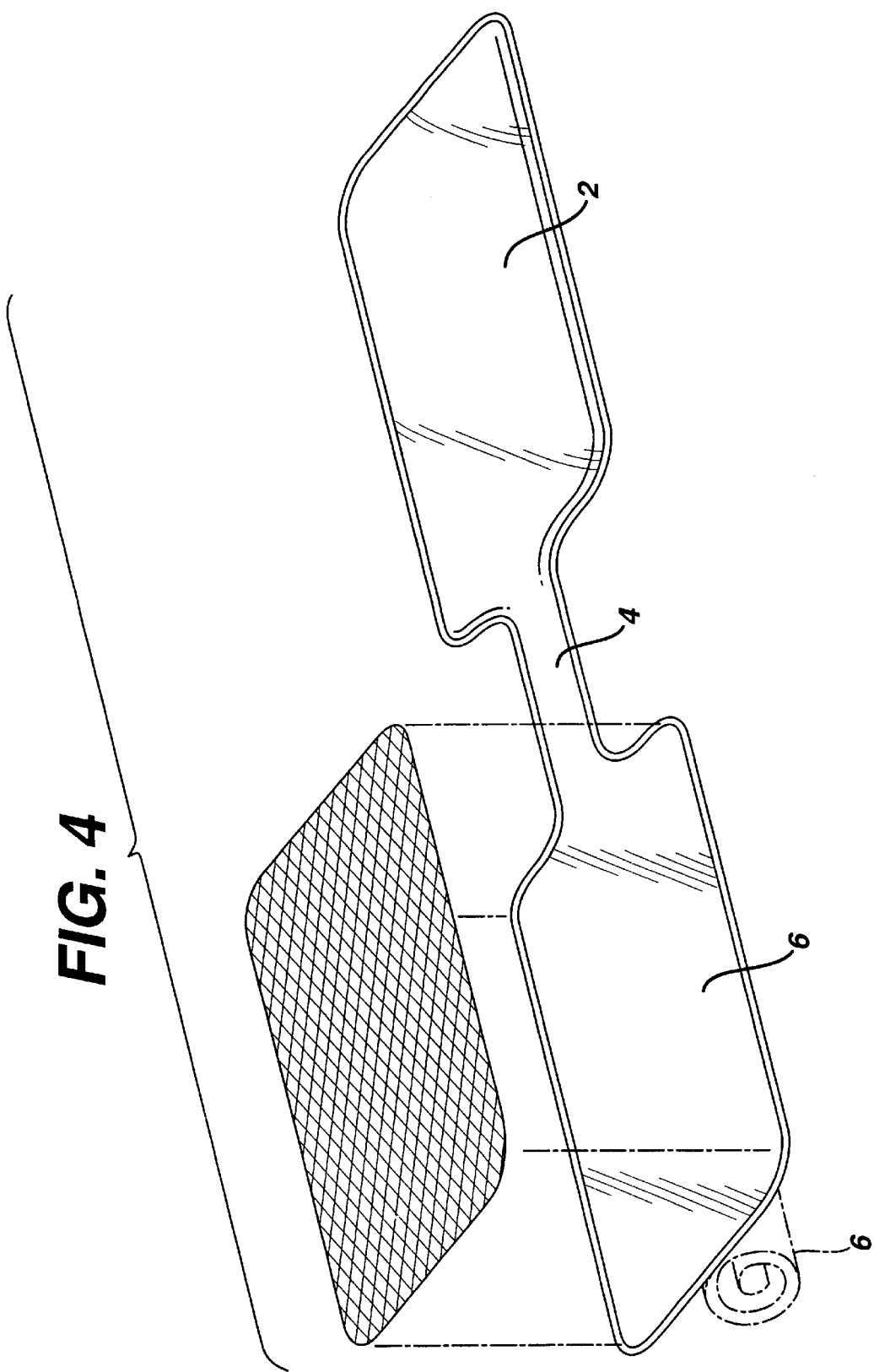

METHOD FOR DEPLOYING MEDICAL TEXTILES

This application is a Divisional Application of U.S. patent application Ser. No. 09/443,882 now U.S. Pat. No. 6,302,897, file on Nov. 19, 1999.

FIELD OF THE INVENTION

The present invention relates to a device for the deployment of medical textiles, more specifically the present device is adapted to deploy mesh devices such as hernia patches.

BACKGROUND OF THE INVENTION

A person may develop a hernia if the abdominal wall is weak and is not capable of keeping the peritoneum in place when larger pressures occur within the abdominal cavity. When a hernia occurs, the peritoneum bulges through a defect within the abdominal wall. Repairs of a hernia defect can be accomplished either anteriorly or posteriorly and may be corrected through the application of sutures, flat mesh prosthesis, prosthetic plugging devices or devices manufactured as multiple layer devices (such as the Prolene Hernia System, manufactured by Ethicon, Inc).

With the advent of minimally invasive surgery, there is a desire to repair the hernia defects through an incision, which is minimal. To this end, anterior approaches that provide posterior repairs have been suggested by Dr. Gilbert and others.

One technique involves making an incision near the site to be repaired, dissecting the tissue down to the peritoneum, dissecting the tissue between the fascia and peritoneum and applying a flat piece of mesh under the site of the defect. The separated tissue layers are held in a retracted position to provide room for the mesh application. The flat mesh is wound onto two instrument shafts (similar to a scroll) and is inserted through the incision. Once in place, the two instrument shafts are rolled in opposite directions to unroll and deposit the mesh at the site of the repair. This technique requires excellent dexterity in order to manipulate the instruments, both to capture the mesh and to unroll it properly.

A second anterior approach suggested by Dr. Gilbert is to make an incision at the site of the defect. The tissue is dissected to the defect. Once the defect is visualized, a sponge is inserted through the defect and the fascial layer is dissected away from the peritoneum. Once the dissection is complete, a two layer mesh prosthetic device (two layers attached at central position) is inserted through the defect and the upper layer is pulled back out of the defect. The surgeon then inserts a finger alongside the central portion of the device and attempts to deploy the lower layer of mesh outward away from the defect into a flattened position on top of the peritoneum. This method does not ensure even distribution of the lower layer since the deployment action is based on a single point of contact with the surgeon's finger.

Applicator devices intended to deploy mesh devices and prosthetic devices with integral opening mechanisms attached have been suggested to improve the ability to deploy the mesh or prosthetic device into a flat condition. U.S. Pat. No. 5,176,692 discloses a balloon applicator device that enables the inflation of a balloon with mesh attached at the site of the defect. The device requires the addition of a means to inflate the balloon once it is placed at the site of the defect to be repaired. This addition of an inflation mechanism extends both the time and cost of the procedure.

U.S. Pat. No. 5,258,000 discloses a means for unfolding the mesh in position through the attachment of an elastic/semi-rigid ring to a piece of flat mesh. The mesh is placed in position in a folded condition and is released. Ideally, the elastic element will exert an opening force to allow the mesh to return to a flattened condition. Unfortunately, the addition of stiffening elements to a flexible piece of mesh as a permanent implant results in patient discomfort and increases the patient awareness of the presence of the device.

SUMMARY OF THE INVENTION

I have discovered a device for the deployment of medical textile devices between layers of tissue composed of a first bladder, a conduit and a second bladder wherein the first bladder is in fluid communications with the second bladder through said conduit and the device is partially filled with a fluid and is sealed.

I have also discovered a process for deploying a medical textile device between two layers of tissue comprising positioning in an undeployed medical device a second bladder which is not completely expanded of a device composed of a first bladder, a conduit and the second bladder wherein the first bladder is in fluid communications with the second bladder through said conduit and the device is partially filled with a fluid and compressing the first bladder thereby expanding the second bladder and deploying the medical textile.

These and other advantages and aspects of the present invention are further explained in the following Detailed Description.

BRIEF DESCRIPTION OF THE FIGURES

FIG. 1 illustrates a preferred embodiment of the present deployment device.

FIG. 2 illustrates a cross section of the preferred embodiment of the present deployment device.

FIG. 3 is a prospective view of one embodiment of the present deployment device with a medical textile device attached.

FIG. 4 is a prospective view of another embodiment of the present deployment device with a medical textile device attached.

DETAILED DESCRIPTION OF THE INVENTION

A preferred embodiment of the present invention is illustrated in FIGS. 1–3. The deployment device 1 is composed of a first bladder 2 that is in fluid communications with a second bladder 6 through at least one conduit 4. The first and second bladders may be one compartment or several individual compartments of any desired shape adapted to deploy the medical textile in question. In a preferred embodiment in an unstressed condition the first bladder 2 (or compartment), has a three-dimensional shape for the containment of a volume of fluid sealed within the system, and the second bladder 6 (or second compartment), in an unstressed condition, remains in an essentially a flattened condition two-dimensional shape. The conduit 4 length is selected based on how and where the medical textile will be deployed. FIG. 3 illustrates one embodiment in which the second bladder 6 is in the shape of a torus with a central passage 12.

The device is preferably manufactured out of a first sheet 8 and second sheet 10 of a biocompatible absorbable or non-absorbable polymeric film material such as polyurethane and PVC. At least one layer of film is thermoformed in one region to create a three dimensional space. A second sheet 10 of film is bonded to the first formed sheet 8 through the use of RF sealing, heat sealing or ultrasonic sealing. During the sealing operation, the thermoformed layer of film is allowed to maintain it's three-dimensional shape. A limited volume of fluid 14 is placed within the device. Suitable fluids that may be used in the device include saline solution, inert gases and air. Preferably sterile air will be trapped within the sealed device since the sealing can be performed in normal ambient conditions. Obviously the volumes of the first bladder 2, the second bladder 6 and the conduit 4 must be adapted to allow the first bladder 2 to transfer sufficient fluid to the second bladder 6 to allow the second bladder 6 to deploy the medical textile device in the desired manner. The second bladder 6 may be any shape suitable to facilitate the deployment of a medical textile device.

The sealed device may be sterilized by gamma sterilization and is then incorporated into the package with an appropriate medical device such as the hernia repair device. Medical textile devices are well known in the art. These devices are generally knitted, woven or nonwoven textile devices made from biocompatible material. One suitable material for medical textile is knitted polypropylene. One suitable medical textile device is described in Ser. No. 09/328,061, filed Jun. 8, 1999 and assigned to Ethicon, Inc. which is hereby incorporated herein by reference. It is preferred that the deployment device is pre-assembled with the passage 12 is placed around the core 20 of the hernia repair device 3 as illustrated in FIG. 3.

The assembly of the deployment device and the hernia repair device is inserted as described by the Gilbert technique. Once the hernia repair device is in the proper position, the first bladder 2 (rectangular section of the deployment device) is squeezed and flattened. This flattening of the three-dimensional shape forces the trapped fluid 14 (i.e. air) into the second bladder 6 of the deployment device 1. Since the polymeric film is flexible, the fluid 14 causes the second bladder 6 to expand into a three-dimensional shape that applies a uniform expansion force against the lower layer 16 of mesh below the fascia. The opening force causes the mesh to move outward into a deployed condition. Once the surgeon is satisfied that the lower layer has deployed properly, the first bladder 2 (rectangular section of the deployment device 1) is released. The force of the tissue causes the trapped fluid 14 (i.e. air) to pass back into the first bladder 2. The device is then pulled off from the core 20 of the hernia repair device and is disposed of.

The second embodiment illustrated in FIG. 4 is intended for applying a flat piece of mesh posteriorly through an anterior approach. The deployment device 1 is manufactured with two rectangular bladders (respectively 2 and 6) connected via conduit 4. The first bladder 2 is preferably thermoformed while the second bladder 6 is preferably not thermoformed. In this procedure the second bladder 6 in a deflated form 1 is placed on a flat piece of mesh 22. The mesh and deflated bladder 6 are rolled into a cylinder and the cylinder is inserted into the location of the repair. Once the cylinder of mesh and deflated bladder is in the proper position, the first bladder 2 (which is substantially inflated) is squeezed. The compression of the first bladder 2 causes the trapped air to be forced into the second bladder 6. This transfer of air causes the second bladder 6 to expand and unfurl. Since the mesh is not attached, it is deposited in place, as it is unrolled with the unfurling section of the expanding device.

I claim:

1. A method of deploying a medical textile through the use of a sealed applicator device having a first compartment and a second compartment in fluid communication with each other, wherein the first compartment, in an unstressed condition, has a three-dimensional shape for the containment of a volume of fluid sealed within the device, and the second compartment, in the unstressed condition, remains in an essentially flattened condition and wherein the medical textile is mated up to the second compartment of the sealed applicator devices the method comprising a) placing the second compartment of the sealed applicator device and the textile posteriorly to a hernial defect, then b) placing the textile position in an essentially deployed position by a transfer of fluid within the sealed applicator device, fluid moving from the first compartment of the sealed applicator device to the second compartment of the applicator device.

* * * * *

UNITED STATES PATENT AND TRADEMARK OFFICE
CERTIFICATE OF CORRECTION

PATENT NO. : 6,685,714 B2
DATED : February 3, 2004
INVENTOR(S) : Robert A. Rousseau It is certified that error appears in the above-identified patent and that said Letters Patent is hereby corrected as shown below:

<u>Column 4,</u>
Line 34, "devices" should read -- device --

Signed and Sealed this

Thirteenth Day of April, 2004

JON W. DUDAS
*Acting Director of the United States Patent and Trademark Office*